US008765765B2

(12) United States Patent
Csongor et al.

(10) Patent No.: US 8,765,765 B2
(45) Date of Patent: Jul. 1, 2014

(54) METABOLITES OF (THIO) CARBAMOYL-CYCLOHEXANE DERIVATIVES

(75) Inventors: Eva Againe Csongor, Budapest (HU); Norbert Antal Kirschner, Tata (HU); Eva Schmidt, Telki (HU); Istvan Gyertyan, Budapest (HU); Bela Kiss, Budapest (HU)

(73) Assignee: Richter Gedeon Nyrt., Budapest (HU)

( * ) Notice: Subject to any disclaimer, the term of this patent is extended or adjusted under 35 U.S.C. 154(b) by 420 days.

(21) Appl. No.: 12/600,826

(22) PCT Filed: May 15, 2008

(86) PCT No.: PCT/HU2008/000046
§ 371 (c)(1),
(2), (4) Date: Dec. 17, 2009

(87) PCT Pub. No.: WO2008/142461
PCT Pub. Date: Nov. 27, 2008

(65) Prior Publication Data
US 2010/0137335 A1 Jun. 3, 2010

(30) Foreign Application Priority Data

May 18, 2007 (HU) .................................. 0700353

(51) Int. Cl.
*A61K 31/495* (2006.01)
*C07D 295/096* (2006.01)
*C07D 295/112* (2006.01)
*C07D 295/24* (2006.01)
*C07D 295/135* (2006.01)

(52) U.S. Cl.
CPC .......... *C07D 295/135* (2013.01); *C07D 295/24* (2013.01)
USPC ...................................... 514/255.03; 544/395

(58) Field of Classification Search
CPC ............. A61K 31/495; C07D 295/096; C07D 295/112
USPC ...................................... 544/395; 514/255.03
See application file for complete search history.

(56) References Cited

U.S. PATENT DOCUMENTS

| 4,666,911 | A | 5/1987 | Fujimura |
| 4,943,632 | A | 7/1990 | Robinson |
| 4,957,921 | A | 9/1990 | Caprathe et al. |
| 5,846,514 | A | 12/1998 | Foster et al. |
| 6,334,997 | B1 | 1/2002 | Foster et al. |
| 6,395,739 | B1 | 5/2002 | Sato |
| 6,489,341 | B1 | 12/2002 | Jerussi |
| 6,528,529 | B1 | 3/2003 | Brann et al. |
| 6,566,550 | B2 | 5/2003 | Lowe, III |
| 6,919,342 | B2 | 7/2005 | Haupt |
| 7,122,576 | B2 | 10/2006 | Plata-Salaman et al. |
| 7,737,142 | B2 * | 6/2010 | Againe Csongor et al. .................. 514/235.8 |
| 7,829,569 | B2 | 11/2010 | Liao et al. |
| 7,875,610 | B2 | 1/2011 | Szalai et al. |
| 7,943,621 | B2 | 5/2011 | Czibula et al. |
| 7,981,897 | B2 | 7/2011 | Bathe et al. |
| 2003/0144285 | A1 | 7/2003 | Brann et al. |
| 2004/0259882 | A1 | 12/2004 | Haupt et al. |
| 2005/0107397 | A1 | 5/2005 | Galambos et al. |
| 2006/0229297 | A1 * | 10/2006 | Csongor et al. ............... 514/218 |
| 2007/0259885 | A1 | 11/2007 | Bathe et al. |
| 2010/0137335 | A1 | 6/2010 | Csongor et al. |
| 2010/0197666 | A1 | 8/2010 | Laszlovsky et al. |
| 2010/0197704 | A1 | 8/2010 | Laszlovsky et al. |
| 2010/0256145 | A1 | 10/2010 | Bak-Jensen et al. |
| 2011/0059980 | A1 | 3/2011 | Oobayashi et al. |
| 2011/0112093 | A1 | 5/2011 | Szalai et al. |
| 2011/0269959 | A1 | 11/2011 | Csongor et al. |
| 2011/0275804 | A1 | 11/2011 | Czibula et al. |
| 2011/0275816 | A1 | 11/2011 | Czibula et al. |

FOREIGN PATENT DOCUMENTS

| EP | 453574 A1 | 10/1991 | | |
| EP | 0431580 | 3/1995 | | |
| JP | 1199977 A | 8/1989 | | |
| JP | 1308284 A | 12/1989 | | |
| JP | 04275280 A | 9/1992 | | |
| JP | 05032586 A | 2/1993 | | |
| JP | 05310745 A | 11/1993 | | |
| WO | WO9107411 A1 | 5/1991 | | |
| WO | WO 97/11070 | 3/1997 | | |
| WO | WO 99/50247 | 10/1999 | | |
| WO | WO 99/67206 | 12/1999 | | |
| WO | WO 01/05763 | 1/2001 | | |
| WO | WO 03/029233 | 4/2003 | | |
| WO | WO 03/064393 | * | 8/2003 | ........... C07D 215/36 |
| WO | WO 2005/012266 | * | 2/2005 | ........... C07D 243/08 |

(Continued)

OTHER PUBLICATIONS

Nassar, et al., Improving the Decision-making Process in the Structural Modification of Drug Candidates: Enhancing Metabolic Stability, DDT vol. 9, No. 23 (2004).*

West, Anthony R., Solid State Chemistry and Its Applications, Wiley, New York, 1988, 358.*

Youdim, The Path from Anti Parkinson Drug Selegiline and Rasagiline to Multifunctional Neuroprotective Anti Alzheimer Drugs Ladostigil and M30, Current Alzheimer Research, 3, 541-550 (2006).*

Aiken, "Pramipexole in psychiatry: A systematic review of the literature," *J. Clin. Psychiatry.*, 68(8):1230-1236, (2007).

(Continued)

*Primary Examiner* — Erich A Leeser
(74) *Attorney, Agent, or Firm* — Fish & Richardson P.C.

(57) ABSTRACT

The present invention relates to metabolites of(thio)-carbamoyl cyclohexane derivatives, particularly, metabolites of trans-4-{2-[4-(2,3-dichlorophenyl)-piperazin-1-yl]-ethyl}-N,N-dimethylcarbamoyl-cyclohexylamine and pharmaceutically acceptable salts thereof, to pharmaceutical compositions containing the same and to their use in the treatment and/or prevention of a conditions which requires modulation of dopamine receptors.

12 Claims, No Drawings

(56) References Cited

FOREIGN PATENT DOCUMENTS

| WO | WO 2005/012266 | 4/2006 | |
|---|---|---|---|
| WO | WO 2006/082456 | 8/2006 | |
| WO | WO 2007/033191 | 3/2007 | |
| WO | WO 2008/139235 | 11/2008 | |
| WO | WO 2008/141135 | * 11/2008 | ........... A61K 31/497 |
| WO | WO 2008/142461 | 11/2008 | |
| WO | WO 2010/009309 | 1/2010 | |

OTHER PUBLICATIONS

Baldessarini and Tarazi, "Pharmacotherapy of Psychosis and Mania," Brunton et al. (eds.), *Goodman and Gilman's The Pharmacological Basis of Therapeutics*, 11th Edition, McGraw Hill, Chapter 18, pp. 462-500, (2005).

Belliotti, et al., "Novel cyclohexyl amides as potent and selective D3 dopamine receptor ligands," *Bioorganic & Medicinal Chemistry Letters*, 7(18):2403-2408, (1997).

Berge et al., "Pharmaceutical salts," *Journal of Pharmaceutical Sciences*, 66(1):1-19 (1977).

Bézard et al., "Attenuation of levodopa-induced dyskinesia by normalizing dopamine D3 receptor function," *Nat. Med.*, 9(6):762-767, (2003).

Burger's Medicinal Chemistry and Drug Discovery. vol. 1. Drug Discovery, 6th Edition. Wiley Interscience. Ed. Donald J. Abraham, ISBN 978-0-471-27090-4, Jan. 2003).

Creese et al., "Species variation in dopamine receptor binding," *Eur. J. Pharmacol.*, 60:55-66, (1979).

Damasio, "Alzheimer's Disease and Related Dementias," *Cecil Textbook of Medicine*, 20th Edition, vol. 2, pp. 1992-1996, (1996).

Dean, Editor. "Recent Advances in the Synthesis and Applications of Radiolabeled Compunds for Drug Discovery and Development," in: *Curr., Pharm. Des.*, 2000; 6(10)] (2000), 110 pp. CAN 133:68895 AN 2000:473538 CAPLUS.

Di Chiara, "Drug addiction as dopamine-dependent associative learning disorder," *Eur. J. Pharmacol.*, 375: 13-30, (1999).

Eli Lilly and Company, "Zyprexa Olanzapine Tablets . . ." MedWatch Safety Alerts for Human Medical Products, FDA [online]. Retrieved rom the Internet< URL: http://www.fda.gov/medwatch/safety/2006/Aug_Pls/Zyprexa_Pl.pdf>, 31 pages, (2004).

Evans, "Synthesis of radiolabeled compounds," *J. Radioanal. Chem.*, 1981, 64(1-2):9-32.

Glase et al., "4-bromo-1-methoxy-N-[2-(4-aryl-1-piperazinyl)ethyl]-2-napthalenecarboxamides: Selective dopamine D3 receptor partial agonists," *Bioorganic & Medicinal Chemistry Letters*, 6(12):1361-1366, 1996.

Greengrass and Bremner, "Binding characteristics of 3H-prazosin to rat brain alpha-adrenergic receptors," *Eur. J. Pharmacol.*, 1979, 55(3):323-326.

Guérémy et al., "2-Amino-6-chloro-4-(N-methylpiperazino)pyrimidines, inhibitors of spiroperidol binding," *J. Med. Chem.*, 25(12):1459-1465, (1982).

Gurevich and Joyce, "Distribution of dopamine D3 receptor expressing neurons in the human forebrain: comparison with D2 receptor expressing neurons," *Neuropsychopharmacology*, 1999, 20:60-80.

Guy, *ECDEU Assessment Manual for Psychopharmacology*. Rockville, Md: US Department of Health, Education, and Welfare, pp. 218-222, 1976. Publication ADM 76-338.

Gyertyan and Saghy, "Effects of dopamine $D_3$ receptor antagonists on spontaneous and agonist-reduced motor activity in NMRI mice and Wistar rats: comparative study with nafadotride, U 99194A and SB 277011," *Behavioural Pharamacology*, vol. 15(4), 2004, pp. 253-262.

Gyertyán and Sághy, "The selective dopamine D3 receptor antagonists, SB 277011-A and S 33084 block haloperidol-induced catalepsy in rats," *Eur. J. Pharmacol.*, 572:171-174, (2007).

Gyertyán et al., "Subnanomolar dopamine D3 receptor antagonism coupled to moderate D2 affinity results in favourable antipsychotic-like activity: Behavioral Data, " [abstract]. *Int. J. Neuropsychopharmacol.*, 2002, 5 Suppl. 1:174.

Heidbreder et al., "The role of central dopamine D3 receptors in drug addiction: a review of pharmacological evidence," *Brain Res. Rev.*, 49:77-105, (2005).

Janssen, "Risperdal Consta (risperidone) Long-Acting Injection," MedWatch Safety Alerts for Human Medical Products, FDA [online] Retrieved from the Internet< URL: http://www.fda.gov/medwatch/safety/2006/Sep_Pls/RisperdalConsta_Pl.pdf>, 39 pages (2006).

Joyce, "Dopamine D3 receptor as a therapeutic target for antipsychotic and antiparkinsonian drugs," *Pharmacol. Therap.*, 90:231-259, (2001).

Kabalka and Varma, "The synthesis of radiolabeled compounds via organometallic intermediates," *Tetrahedron*, 1989, 45(21):6601-6621.

Kay et al., "The positive and negative syndrome scale (PANSS) for schizophrenia," *Schizophr. Bull.*, 1987, 13:261-276.

Keck, "The management of acute mania," *British Medical Journal*, 2003, 327(7422):1002-1003.

Laszy et al., "Dopamine D3 receptor antagonists improve the learning performance in memory impaired rats," *Psychopharmacol.*, 179(3):567-575, (2005).

Layzer, Degenerative Diseases of the Nervous System, *Cecil Textbook of Medicine*, 20th Edition, vol. 2, pp. 2050-2057, (1996).

Le Foll et al., "Dopamine D3 receptor ligands for the treatment of tobacco dependence," *Expert Opin Investig Drugs*, 16(1):45-57, (2007).

Levant and McCarson, "D(3) dopamine receptors in rat spinal cord: implications for sensory and motor function," *Neurosci. Lett.*, 303:9-12 (2001).

Levant et al., "Dopamine $D_3$ receptor: relevance for the drug treatment of Parkinson's disease," *CNS Drugs*, 1999, 12:391-402.

Levant, "The D3 dopamine receptor: neurobiology and potential clinical relevance," *Pharmacol. Rev.*, 49(3):231-252, (1997).

Maj et al., "Effect of antidepressant drugs administered repeatedly on the dopamine D3 receptors in the rat brain," *Eur. J. Pharmacol.* 351:31-37, (1998)

Millan et al., "S33084, a novel, potent, selective, and competitive antagonist at dopamine D(3)-receptors: II. Functional and behavioral profile compared with GR218,231 and L741,626," *J. Pharmacol. Exp. Ther.*, 2000, 293:1063-1073.

Millan et al., "The dopamine D3 receptor antagonist, (+)-S 14297, blocks the cataleptic properties of haloperidol in rats," *Eur. J. Pharmacol.*, 321:R7-R9, (1997).

Montgomery and Asberg, "A new depression scale designed to be sensitive to change," Br. J. Psychiatry, 1979, 134:382-389.

Nyberg et al., "Positron emission tomography of in-vivo binding characteristics of atypical antipsychotic drugs. Review of D2 and 5-HT2 receptor occupancy studies and clinical response," *Br. J. Psychiatry. Suppl.*, May 1996, 29:40-44.

Pacher and Kecskeméti, "Cardiovascular side effects of new antidepressants and antipsychotics: new drugs, old concerns?" *Curr. Pharm. Des.*, 2004, 10(20):2463-2475.

Papp and Wieronska, "Antidepressant-like activity of amisulpride in two animal models of depression," *J. Psychopharmacol.*, 14:46-52, (2000).

Pilla et al., "Selective inhibition of cocaine-seeking behaviour by a partial dopamine D3 receptor agonist," *Nature*, 400:371-375, (1999).

Reavill et al., "Pharmacological actions of a novel, high-affinity, and selective human dopamine D(3) receptor antagonist, SB-277011-A," *A. J. Pharmacol. Exp. Ther.*, 2000, 294:1154-1165.

Rogó et al., "Anxiolytic-like effect of nafadotride and PNU 99194A, dopamine D3 receptor antagonists in animal models," *Pol J Pharmacol.*, 52(6):459-462, (2000).

Russell, "Neurobiology of animal models of attention-deficit hyperactivity disorder," *J. Neurosci. Methods* 161:185-198, (2007).

Sachs, "Unmet clinical needs in bipolar disorder," *J. Clin. Psychopharmacol.*, 2003, 23(3 Suppl 1):S2-S8.

Sautel et al., "Nafadotride, a potent preferential dopamine D3 receptor antagonist, activates locomotion in rodents," *J. Pharmacol. Exp. Ther.*, 1995, 275:1239-1246.

Schwartz et al., "Dopamine D3 receptor: basic and clinical aspects," *Clin. Neuropharmacol.*, 16(4):295-314, (1993).

(56) References Cited

OTHER PUBLICATIONS

Schwartz et. al., "Possible implications of the dopamine D(3) receptor in schizophrenia and in antipsychotic drug actions," Brain Res. Rev., 31(2-3):277-287, (2000).
Seeman, "Brain dopamine receptors" Pharmacological Reviews, 32(3): 229-313 (1980).
Shalev et al., "Neurobiology of relapse to heroin and cocaine seeking: a review.," Pharmacol. Rev. 54 (1), 1-42, (2002).
Sigala et al., "Opposite effects of dopamine $D_2$ and $D_3$ receptors on learning and memory in the rat," Eur. J. Pharmacol., 1997, 336:107-112.
Smith et al., "The dopamine D3/D2 receptor agonist 7-OH-DPAT induces cognitive impairment in the marmoset," Pharmacol. Biochem. Behav., 1999, 63:201-211.
Sokoloff et al., "Molecular cloning and characterization of a novel dopamine receptor (D3) as a target for neuroleptics," Nature, 347:146-151, (1990).
Souillac, et al., Characterization of Delivery Systems, Differential Scanning Calorimetry, pp. 217-218 (in Encyclopedia of Controlled Drug Delivery, 1999, John Wiley & Sons, pp. 212-227).
Stahl and Grady, "A critical review of atypical antipsychotic utilization: comparing monotherapy with polypharmacy and augmentation," Curr. Med. Chem., 2004, 11:313-27.
Stahl, Essential Psychopharmacology: Neuroscientific Basis and Practical Applications, 2nd ed., p. 409, Cambridge University Press, pp. 409-414, (2000).
Steiner et al., "D3 dopamine receptor-deficient mouse: evidence for reduced anxiety," Physiol Behav., 63(1):137-141, (1997).
Stemp et al., "Design and synthesis of trans-N-[4-[2-(6-cyano-1,2,3,4-tetrahydroisoquinolin-2-yl)ethyl]cyclohexyl]-4-quinolinecarboxamide (SB-277011): A potent and selective dopamine D(3) receptor antagonist with high oral bioavailability and CNS penetration in the rat," J. Med. Chem., 43(9):1878-1885, (2000).
Tada et al., "Combined treatment of quetiapine with haloperidol in animal models of antipsychotic effect and extrapyramidal side effects: comparison with risperidone and chlorpromazine," Psychopharmacology (Berl), 176(1):94-100, (2004).
Thanos et al., "The effects of two highly selective dopamine D3 receptor antagonists (SB-277011A and NGB-2904) on food self-administration in a rodent model of obesity," Pharmacol Biochem Behav. 89: 499-507, (2008).
Ukai et al., "Effects of the dopamine D3 receptor agonist, R(+)-7-hydroxy-N,N-di-n-propyl-2-aminotetralin, on memory processes in mice," Eur. J. Pharmacol., 1997, 324:147-151.
Ulrich, Chapter 4: Crystallization, Kirk-Othmer Encyclopedia of Chemical Technology, 7 pages, (Aug. 2002).
van der Kooij and Glennon, "Animal models concerning the role of dopamine in attention-deficit hyperactivity disorder," Neuroscience and Biobehavioral Reviews, 31: 597-618, (2005).
Willner et al., "Dopaminergic mechanism of antidepressant action in depressed patients," J. Affective Disorders 86: 37-45, (2005).
Wong and Van Tol, "Schizophrenia: from phenomenology to neurobiology," Neurosci. Biobehav. Rev., 27(3):269-306, (2003).

World Health Organization, World Health Report 2001, "Mental Health: New Understanding, New Hope." http://www.who.int/whr/2001/en/2001.
Wyatt and Henter, "An economic evaluation of manic-depressive illness—1991," Soc. Psychiatry Psychiatr. Epidemiol., 1995, 30(5):213-219.
International Search Report for PCT/HU2008/000046, mailed Sep. 22, 2008, 2 pages.
International Preliminary Report on Patentability and Written Opinion for PCT/US2008/000046, mailed Nov. 24, 2009, 9 pages.
Goodwin and Jamison, "Medical Treatment of Acute Bipolar Depression," Manic-depressive illness, New York: Oxford University Press, pp. 642-647.
Gurevich et al., "Mesolimbic dopamine D3 receptors and use of antipsychotics in patients with schizophrenia. A postmortem study." Arch Gen Psychiatry., 54(3):225-232, 1997.
Lehman et al., "Practice guideline for the treatment of patients with schizophrenia, second edition," Am. J. Psychiatry, 161(2 Suppl):1-56, 2004.
Mueser and McGurk, "Schizophrenia," Lancet, 363:2063-2072, 2004.
Müller-Oerlinghausen et al., "Bipolar disorder," Lancet, 359(9302):241-247, 2002.
Schwartz et al., "Dopamine D3 receptor: basic and clinical aspects," Clin Neuropharmacol., 16(4):295-314, 1993.
Seeman, "Antipsychotic drugs, dopamine receptors and schizophrenia," Clin. Neurosci. Res., 1:53-60, 2001.
Shafer and Levant, "The D3 dopamine receptor in cellular and organismal function," Psychopharmacology (Berl), v, 135:1-16, 1998.
Waters et al., "Differential effects of dopamine D2 and D3 receptor antagonists in regard to dopamine release, in vivo receptor displacement and behavior," J. Neural. Transm. Gen. Sect., 98:39-55, 1994.
Zink et al., "Combination of amisulpride and olanzapine in treatment-resistant schizophrenic psychoses," Eur. Psychiatry, 19:56-58, 2004.
Morissette et al; High-throughput crystallization: polymorphs, salts, co-crystals and solvates of pharmaceutical solids; Adv Drug Deliv Rev; Feb. 2004; 56(3):275-300.
Pacher and Kecskeméti; Cardiovascular side effects of new antidepressants and antipsychotics: new drugs, old concerns?; Curr. Pharm. Des.; 2004; 10(20):2463-2475.
Han; Advances in Characterization of Pharmaceutical Hydrates; Trends in Bio/Pharmaceutical Industry; 2006; 2(3): 25-29.
Nassar et al; Improving the decision-making process in structural modification of drug candidates: reducing toxicity; Drug Discov Today; Dec. 2004; 9(24):1055-1064.
Vippagunta et al; Crystalline Solids; Advanced Drug Delivery Reviews; 2001; 48(1):3-26.
Youdim; The path from anti Parkinson drug selegiline and rasagiline to multifunctional neuroprotective anti Alzheimer drugs ladostigil and m30; Curr Alzheimer Res.; 2006; 3(5):541-550.
Young et al; A rating scale for mania: reliability, validity and sensitivity; The British Journal of Psychiatry; 1978; 133:429-435.

* cited by examiner

US 8,765,765 B2

METABOLITES OF (THIO) CARBAMOYL-CYCLOHEXANE DERIVATIVES

CROSS-REFERENCE TO RELATED APPLICATIONS

This application is a National Stage application under 35 U.S.C. §371 and claims benefit of International Application No. PCT/HU2008/000046 having an International Filing Date of May 15, 2008, which claims the benefit of priority of HU P0700353 having a filing date of May 18, 2007.

FIELD OF THE INVENTION

The present invention relates to metabolites of (thio)-carbamoyl cyclohexane derivatives, particularly, metabolites of trans-4-{2-[4-(2,3-dichlorophenyl)-piperazin-1-yl]-ethyl}-N,N-dimethylcarbamoyl-cyclohexylamine and pharmaceutically acceptable salts thereof, to pharmaceutical compositions containing the same and to their use in the treatment and/or prevention of a conditions which requires modulation of dopamine receptors.

BACKGROUND OF THE INVENTION

U.S. Patent Publication No. 2006/0229297 discloses (thio)-carbamoyl-cyclohexane derivatives that are $D_3$ and $D_2$ dopamine receptor subtype preferring ligands, having the formula (I):

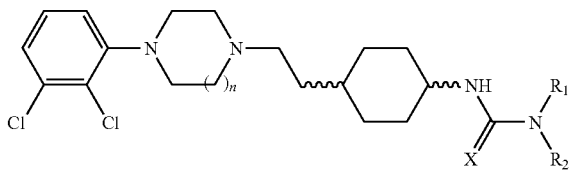

(I)

wherein $R_1$, $R_2$, X, and n are as defined therein.

One particular compound disclosed in the Hungarian patent application No. P0700339 is trans-4-{2-[4-(2,3-dichlorophenyl)-piperazin-1-yl]-ethyl}-N,N-dimethylcarbamoyl-cyclohexylamine hydrochloride, which is also known as trans-1{4-[2-[4-(2,3-dichlorophenyl)-piperazin-1-yl]-ethyl]-cyclohexyl}-3,3-dimethyl-urea hydrochloride, the structural formula for which is shown below:

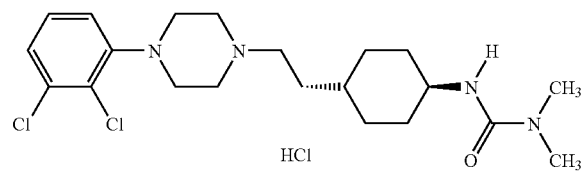

Trans-4-{2-[4-(2,3-dichlorophenyl)-piperazin-1-yl]-ethyl}-N,N-dimethylcarbamoyl-cyclohexylamine hydrochloride is an orally active and very potent dopamine $D_3/D_2$ receptor antagonist, which binds with significantly higher potency to $D_3$ than $D_2$ receptors. The $D_3$ receptor antagonism is about one order of magnitude greater than the $D_2$ receptor antagonism, which is believed to counteract some of the extrapyramidal side effects produced by $D_2$ receptor antagonists. Another unique feature of trans-4-{2-[4-(2,3-dichlorophenyl)-piperazin-1-yl]-ethyl}-N,N-dimethylcarbamoyl-cyclohexylamine hydrochloride is that in vivo it acts as a "dopamine system stabilizer." In this regard, it has preferential dopaminergic actions in the limbic regions and displays both (partial) agonist and antagonist activity on biosynthesis (and release) modulating presynaptic $D_2$ receptors depending on the functional status of the particular dopaminergic system.

These compounds have high or very high affinity for dopamine $D_3$ receptors and moderate to high affinity to dopamine $D_2$ receptors always in such a combination that the $D_3$ affinity is 5 to 200 fold higher than the $D_2$ affinity. In addition, the compounds have even higher selectivity over other receptors, such as alpha-1 receptors. The dual (i.e. $D_3$ and $D_2$) receptor functional antagonism coupled in the above mentioned particular proportion is especially important as it allows the simultaneous manifestation of the beneficial effects of modulation of both the $D_3$ and $D_2$ receptors, however, without the appearance of the known disadvantages of each individual receptor action.

In addition to the increased relative affinity to dopamine $D_3$ to $D_2$, trans-4-{2-[4-(2,3-dichlorophenyl)-piperazin-1-yl]ethyl}-N,N-dimethylcarbamoyl-cyclohexylamine hydrochloride has a low potency at other receptor sites such as the $5\text{-HT}_{2C}$, histamine $H_1$, and adrenergic receptor sites, which suggest a lower potential for side effects such as extrapyramidal symptoms (EPS) and body weight gain.

These compounds are useful in the treatment and/or prevention of pathological conditions which require the modulation of dopamine receptors.

SUMMARY OF THE INVENTION

The present invention relates to metabolites of (thio)-carbamoyl cyclohexane derivatives, particularly metabolites of trans-4-{2-[4-(2,3-dichlorophenyl)-piperazin-1-yl]-ethyl}-N,N-dimethylcarbamoyl-cyclohexylamine and pharmaceutically acceptable salts thereof, to pharmaceutical compositions containing the same and to their use in therapy and/or prevention of a conditions which requires modulation of dopamine receptors.

DETAILED DESCRIPTION OF THE INVENTION

The present invention relates to isolated and/or purified and/or synthetized metabolites of compounds of formula (I):

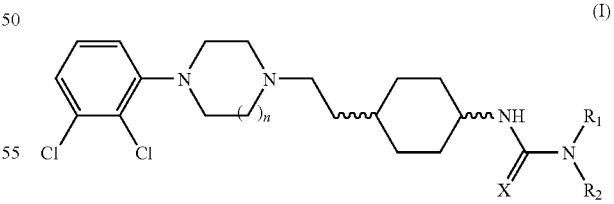

(I)

wherein $R_1$ and $R_2$ are each, independently hydrogen, alkyl, alkenyl, aryl, cycloalkyl, aroyl, or $R_1$ and $R_2$ form a heterocyclic ring with the adjacent nitrogen atom;

X is O or S;

n is 1 or 2;

and/or geometric isomers and/or stereoisomers and/or diastereomers and/or salts and/or hydrates and/or solvates and/or polymorphs thereof.

In certain embodiments, the present invention relates to compounds of formulae (II) and/or (III):

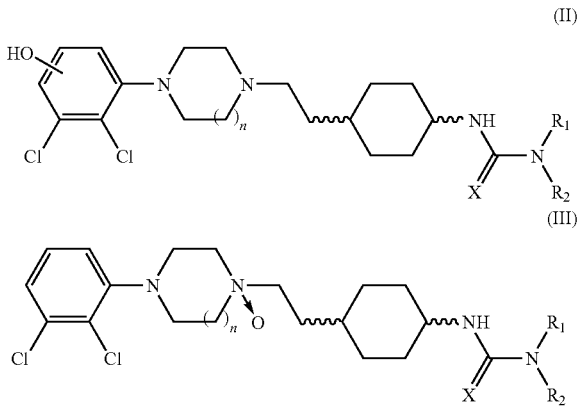

wherein

R₁ and R₂, are each, independently, hydrogen, alkyl, alkenyl, aryl, cycloalkyl, or aroyl, or R₁ and R₂ independently form a heterocyclic ring with the adjacent nitrogen atom;

X is O or S;

n is 1 or 2;

and/or geometric isomers and/or stereoisomers and/or diastereomers and/or salts and/or hydrates and/or solvates and/or polymorphs thereof.

In one embodiment, the compounds of formulae (II) and/or (III) are in purified form. In another embodiment, the compounds of formulae (II) and/or (III) are present in substantially pure form. In a further embodiment, the compounds of formulae (II) and/or (III) are isolated and/or synthetized.

In one embodiment, compounds of formula (II) are represented by formula (IIa):

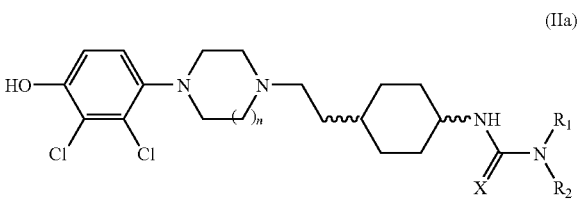

wherein R₁, R₂, X and n are as defined above for formula (II).

In certain embodiments, when R₁ and/or R₂ represent alkyl, the alkyl moiety is a substituted or unsubstituted saturated hydrocarbon radical which may be straight-chain or branched-chain and contains about 1 to about 6 carbon atoms (particularly, 1 to 4 carbon atoms), and is optionally substituted with one or more $C_{1-6}$ alkoxycarbonyl, aryl (e.g., phenyl) or ($C_{1-6}$ alkoxycarbonyl)-$C_{1-6}$ alkyl groups, or combinations thereof.

In additional embodiments, R₁ and R₂ form a heterocyclic ring with the adjacent nitrogen atom, which may be a saturated or unsaturated, optionally substituted, monocyclic or bicyclic ring, which may contain further heteroatoms selected from O, N, or S. For example, the heterocyclic ring can be pyrrolidine, piperazine, piperidine or morpholine.

In additional embodiments, when R₁ and/or R₂ represent alkenyl, the alkenyl moiety may have 2 to 7 carbon atoms and 1 to 3 double bonds.

In additional embodiments, when R₁ and/or R₂ represent aryl, the aryl moiety may be selected from an optionally substituted mono-, bi- or tricyclic aryl, such as, but not limited to, phenyl, naphthyl, fluorononyl, or anthraquinonyl group (e.g., phenyl or naphthyl). The aryl moiety may be substituted with one or more $C_{1-6}$ alkoxy, trifluoro-$C_{1-6}$ alkoxy, $C_{1-6}$ alkoxycarbonyl, $C_{1-6}$ alkanoyl, aryl, $C_{1-6}$ alkylthio, halogen, cyano groups or combinations thereof.

In additional embodiments, when R₁ and/or R₂ represent cycloalkyl, the cycloalkyl moiety may be selected from an optionally substituted mono-, bi- or tricyclic cycloalkyl group, such as cyclohexyl or adamantyl.

In additional embodiments, when R₁ and/or R₂ represent aroyl the aryl moiety therein is as defined above, e.g., phenyl.

In certain embodiments, the present invention relates to compounds of formulae (II) and/or (III) wherein R₁ and R₂ are each, independently hydrogen, $C_{1-6}$ alkyl with straight or branched chain optionally substituted with one or more $C_{1-6}$ alkoxycarbonyl, aryl or ($C_{1-6}$ alkoxycarbonyl)-$C_{1-6}$ alkyl group, $C_{2-7}$ alkenyl with 1 to 3 double bonds, a mono-, bi- or tricyclic aryl optionally substituted with one or more $C_{1-6}$ alkoxy, trifluoro-$C_{1-6}$-alkoxy, $C_{1-6}$ alkoxycarbonyl, $C_{1-6}$ alkanoyl, aryl, $C_{1-6}$ alkylthio, halogen, cyano, an optionally substituted mono-, bi- or tricyclic cycloalkyl, aroyl, or R₁ and/or R₂ form a heterocyclic ring with the adjacent nitrogen atom, which may be saturated or unsaturated optionally substituted monocyclic or bicyclic ring, which may contain further heteroatoms selected from O, N, or S;

X is O or S; and n is 1 or 2.

In further embodiments, the present invention relates to compounds of formula (II) and/or (III) wherein R₁ and R₂ are each, independently hydrogen, $C_{1-6}$ alkyl with straight or branched chain and optionally substituted with one or more $C_{1-6}$ alkoxycarbonyl, phenyl or ($C_{1-6}$ alkoxycarbonyl)-$C_{1-6}$ alkyl, $C_{2-7}$ alkenyl with 1 double bond, phenyl or naphthyl optionally substituted with one or more $C_{1-6}$ alkoxy, trifluoro-$C_{1-6}$ alkoxy, $C_{1-6}$ alkoxycarbonyl, $C_{1-6}$ alkanoyl, aryl, $C_{1-6}$ alkylthio, halogen, cyano, cyclohexyl, adamantyl, benzoyl, or R₁ and/or R₂ form a heterocyclic ring with the adjacent nitrogen atom, which may be saturated optionally by $C_{1-6}$ alkyl or hydroxy substituted monocyclic ring, which may contain further heteroatoms selected from O or N;

X is O or S; and n is 1 or 2.

In additional embodiments, the present invention relates to compounds of formulae (II) and/or (III) wherein R₁ and R₂ are each, independently hydrogen, $C_{1-6}$ alkyl with straight or branched chain optionally substituted with $C_{1-6}$ alkoxycarbonyl or phenyl, allyl, phenyl optionally substituted with one or more $C_{1-6}$ alkoxy, cyano or $C_{1-6}$ alkanoyl, cyclohexyl, or R₁ and/or R₂ form with the adjacent nitrogen atom an optionally by $C_{1-6}$ alkyl or hydroxy substituted pyrrolidine, piperazine, piperidine or morpholine ring;

X is O or S; and n is 1.

In additional embodiments, R₁ and R₂ are each, independently, selected from hydrogen or alkyl (e.g., methyl).

In further embodiments, the present invention relates to compounds of formulae (II) and/or (III) wherein R₁ and R₂ are each, independently, hydrogen or methyl (e.g., R₁ and R₂ are both hydrogen, one of R₁ and R₂ is hydrogen and the other is methyl, R₁ and R₂ are both methyl).

In a further embodiment, the present invention relates to metabolites of trans-4-{2-[4-(2,3-dichlorophenyl)-piperazin-1-yl]-ethyl}-N,N-dimethylcarbamoyl-cyclohexylamine, and/or geometric isomers and/or stereoisomers and/or diastereomers and/or salts and/or hydrates and/or solvates and/or polymorphs thereof.

In certain embodiments, the metabolite can be a glucuronide, an oxidation compound, a monohydroxylated compound or a sulphate conjugate.

In one embodiment, the metabolites of trans-4-{2-[4-(2,3-dichlorophenyl)-piperazin-1-yl]-ethyl}-N,N-dimethylcarbamoyl-cyclohexylamine are present in substantially pure form.

In another embodiment, the metabolites of trans-4-{2-[4-(2,3-dichlorophenyl)-piperazin-1-yl]-ethyl}-N,N-dimethylcarbamoyl-cyclohexylamine are isolated.

In another embodiment, the metabolites of trans-4-{2-[4-(2,3-dichlorophenyl)-piperazin-1-yl]-ethyl}-N,N-dimethylcarbamoyl-cyclohexylamine are in purified form.

In another embodiment, the metabolites of trans-4-{2-[4-(2,3-dichlorophenyl)-piperazin-1-yl]-ethyl}-N,N-dimethylcarbamoyl-cyclohexylamine are synthetized.

In another embodiment, the metabolite of the present invention is selected from:

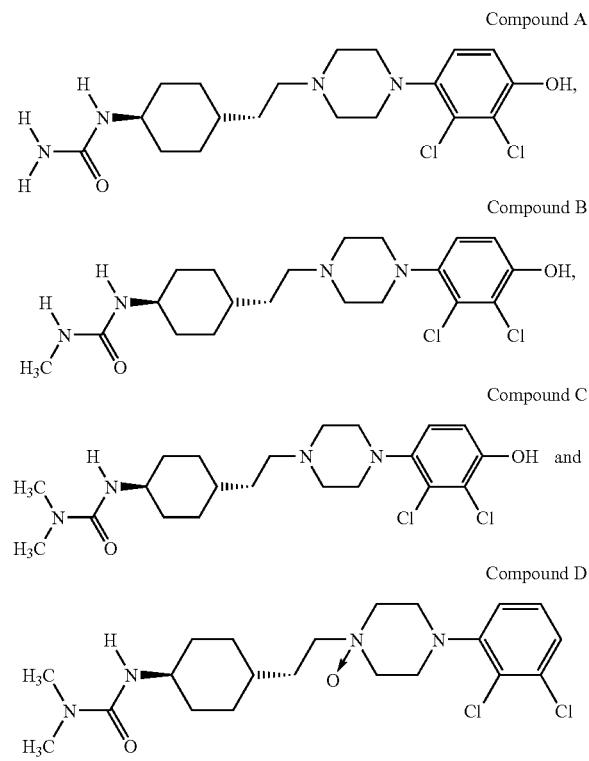

and/or geometric isomers and/or stereoisomers and/or diastereomers and/or salts and/or hydrates and/or solvates and/or polymorphs thereof.

Pharmaceutically Acceptable Salts

Pharmaceutically acceptable salts include those obtained by reacting the main compound, functioning as a base with an inorganic or organic acid to form a salt, for example, salts of hydrochloric acid, sulfuric acid, phosphoric acid, methane sulfonic acid, camphor sulfonic acid, oxalic acid, maleic acid, succinic acid, citric acid, formic acid, hydrobromic acid, benzoic acid, tartaric acid, fumaric acid, salicylic acid, mandelic acid, and carbonic acid. Pharmaceutically acceptable salts also include those in which the main compound functions as an acid and is reacted with an appropriate base to form, e.g., sodium, potassium, calcium, magnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts can be prepared by reacting the compounds of the invention with the appropriate base via a variety of known methods.

The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and In one embodiment, the pharmaceutically acceptable salt is a hydrochloride salt.

One of ordinary skill in the art will also recognize that some of the compounds useful in the present invention can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds. The use of such polymorphs is within the scope of the present invention.

One of ordinary skill in the art will further recognize that some of the compounds useful in the present invention can exist in different solvate forms. Solvates of the compounds of the invention may also form when solvent molecules are incorporated into the crystalline lattice structure of the compound molecule during the crystallization process. For example, suitable solvates include hydrates, e.g., monohydrates, dihydrates, sesquihydrates, and hemihydrates. The use of such solvates is within the scope of the present invention.

One of ordinary skill in the art will further recognize that the compounds of formulae (II) and/or (III) can exist in the form of cis and trans isomers with respect to the configuration of the cyclohexane ring. These and their mixtures are likewise within the scope of the present invention. The compounds of the invention are preferably in trans configuration.

Certain compounds of formulae (II) and/or (III) when the compound contains $C_{2-7}$ alkenyl group can exist in the form of cis- and/or trans-isomers. These are likewise within the scope of the present invention including all such isomers and the mixtures thereof.

Certain compounds of formulae (II) and/or (III) can exist as stereoisomers and diastereomers, too. These and the mixtures thereof are likewise within the scope of the present invention.

As the invention relates also to the salts of compounds of formulae (II) and/or (III) formed with acids, especially the salts formed with pharmaceutically acceptable acids, the meaning of a compound of formulae (II) and/or (III) is independently either the free base or the salt even if it is not referred to separately.

One of ordinary skill in the art will recognize that compounds of formulae (II) and/or (III) can exist in different tautomeric and geometrical isomeric forms. All of these compounds, including cis isomers, trans isomers, diastereomic mixtures, racemates, nonracemic mixtures of enantiomers, substantially pure, and pure enantiomers, are within the scope of the present invention. Substantially pure enantiomers contain no more than 5% w/w of the corresponding opposite enantiomer, preferably no more than 2%, most preferably no more than 1%.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical and/or chemical differences by methods known to those skilled in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of formulae (II) and/or (III) can likewise be obtained by utilizing optically active starting materials in chiral synthesis processes under reaction conditions which do not cause racemization.

In addition, one of ordinary skill in the art will recognize that the compounds can be used in different enriched isotopic forms, e.g., enriched in the content of $^2H$, $^3H$, $^{11}C$, $^{13}C$ and/or $^{14}C$. In one particular embodiment, the compounds are deuterated. Such deuterated forms can be made by the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] (2000), 110 pp. CAN 133:68895 AN 2000:473538 CAPLUS; Kabalka, George W.; Varma, Rajender S. The synthesis of radiolabeled compounds via organometallic intermediates. Tetrahedron (1989), 45(21), 6601-21, CODEN: TETRAB ISSN:0040-4020. CAN 112:20527 AN 1990:20527 CAPLUS; and Evans, E. Anthony. Synthesis of radiolabeled compounds, J. Radioanal. Chem. (1981), 64(1-2), 9-32. CODEN: JRACBN ISSN:0022-4081, CAN 95:76229 AN 1981:476229 CAPLUS.

Where applicable, the present invention also relates to useful forms of the compounds as disclosed herein, such as base free forms, and pharmaceutically acceptable salts or prodrugs of all the compounds of the present invention for which salts or prodrugs can be prepared.

Compositions

The present invention also includes pharmaceutical compositions of the metabolites of the present invention, containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

Administration of the compounds of formulae (II) and/or (III) of the present invention may be accomplished according to patient needs, for example, orally, nasally, parenterally (subcutaneously, intraveneously, intramuscularly, intrasternally and by infusion) by inhalation, rectally, vaginally, topically and by ocular administration.

Various solid oral dosage forms can be used for administering the compounds of formulae (II) and/or (III) of the invention including such solid forms as tablets, gelcaps, capsules, caplets, granules, lozenges and bulk powders. The polymorphs and solvates of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering the compounds of formulae (II) and/or (III), including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The polymorphs and solvates of the present invention may be injected, for example, intravenously, in the form of an isotonic sterile solution. Other preparations are also possible.

Suppositories for rectal administration of the compounds of formulae (II) and/or (III) of the present invention can be prepared by mixing the compound with a suitable excipient such as cocoa butter, salicylates and polyethylene glycols. Formulations for vaginal administration can be in the form of a pessary, tampon, cream, gel, past foam, or spray formula containing, in addition to the active ingredient, such suitable carriers as are known in the art.

For topical administration, the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for treatment of disorders of the respiratory tract, the compounds according to the invention can be administered by inhalation in the form of a powder (e.g., micronized) or in the form of atomized solutions or suspensions. The aerosol formulation can be placed into a pressurized acceptable propellant.

The invention also provides the use of a compound of present invention in the manufacture of a medicament for the treatment of conditions which require modulation of a dopamine receptor, particularly, a dopamine $D_3$ and/or $D_2$ receptor.

The present invention further provides methods for treating a condition which requires modulation of a dopamine receptor, particularly, a dopamine $D_3$ and/or $D_2$ receptor. In further embodiments, the present invention provides methods for treating a condition which requires modulation of a dopamine $D_3$ and/or $D_2$ receptor utilizing one or more compounds of the present invention.

Dysfunction of the dopaminergic neurotransmitter system is involved in the pathology of several neuropsychiatric and neurodegenerative disorders, such as schizophrenia, drug abuse and Parkinson's disease, respectively. The effect of dopamine is mediated via at least five distinct dopamine receptors belonging to the $D_1$-($D_1$, $D_5$) or the $D_2$-($D_2$, $D_3$, $D_4$) families. $D_3$ receptors have been shown to have characteristic distribution in the cerebral dopaminergic systems. Namely, high densities were found in certain limbic structures, such as nucleus accumbens and islands of Calleja. Therefore, preferential targeting of the $D_3$ receptors may be a promising approach for more selective modulation of dopaminergic functions and consequently for successful therapeutic intervention in several abnormalities, such as schizophrenia, emotional or cognitive dysfunctions and addiction (see, e.g., Sokoloff, P. et al.: Nature, 1990, 347, 146; Schwartz, J. C., et al.: Clin. Neuropharmacol. 1993, 16, 295; Levant, B.: Pharmacol. Rev. 1997, 49, 231), addiction (see, e.g., Pilla, C. et al.: Nature 1999, 400, 371) and Parkinson's disease (see, e.g., Levant, B. et al.: CNS Drugs 1999, 12, 391) or pain (see, e.g., Levant, B. et al.: Neurosci. Lett. 2001, 303, 9).

The dopamine $D_2$ receptors are widely distributed in the brain and are known to be involved in numerous physiological functions and pathological states. $D_2$ antagonists are widely used drugs as antipsychotics, for example. However, it is also well known that massive antagonism of the $D_2$ receptors leads to unwanted side-effects such as extrapyramidal motor symptoms, psychomotor sedation or cognitive disturbances. These side effects seriously restrict the therapeutic utilization of $D_2$ antagonist compounds. (Wong A. H. C. et al.: Neurosci. Biobehay. Rev. 2003, 27, 269.)

In a further aspect, the present invention provides a method of treating conditions which require preferential modulation of dopamine $D_3$ and/or $D_2$ receptors, for example psychoses (e.g. schizophrenia, schizo-affective disorders), cognitive impairment accompanying schizophrenia, mild-to-moderate cognitive deficits, dementia, psychotic states associated with dementia, psychotic depression, mania, paranoid and delusional disorders, obsessive compulsive disorders, dyskinetic disorders such as Parkinson's disease, neuroleptic induced parkinsonism, tardive dyskinesia, eating disorders (e.g. bulimia nervosa), attention deficit disorders, hyperactivity disorders in children, depression, anxiety, sexual dysfunction, sleep disorders, emesis, aggression, autism and drug abuse, which comprises administering to a subject in need thereof an effective amount of a compound and/or composition of the present invention.

A preferred use for $D_3/D_2$ antagonists with $D_3$ preference according to the present invention is in the treatment of schizophrenia, schizo-affective disorders, cognitive impairment accompanying schizophrenia, mild-to-moderate cognitive deficits, dementia, psychotic states associated with dementia, psychotic depression, mania, paranoid and delusional disorders, obsessive compulsive disorders, dyskinetic disorders such as Parkinson's disease, neuroleptic induced parkinsonism, depression, anxiety, drug abuse (e.g. cocaine, alcohol, nicotine abuse).

The particular combination of the two receptor-actions described above allows the simultaneous manifestation of the beneficial actions of both the $D_3$ antagonism (e.g. cognitive enhancer effect, inhibition of extrapyramidal motor symptoms, inhibitory action on drug abuse) and the $D_2$ antagonism (e.g. antipsychotic effect). Furthermore, the same combination surprisingly results in canceling out the disadvantageous features of $D_2$ antagonism (e.g. extrapyramidal symptoms, psychomotor sedation, cognitive disturbances).

The term "substantially pure" means a compound having a purity greater then, e.g., about 90% by weight, for example, greater than about 91% by weight, greater than about 92% by weight, greater than about 93% by weight, greater than about 94% by weight, greater than about 95% by weight, greater than about 96% by weight, greater than about 97% by weight, greater than about 97.5% by weight, greater than about 98% by weight, greater than about 99% by weight, greater than about 99.5% by weight, or greater than about 99.9% by weight. One of ordinary skill in the art would readily appreciate various methods by which the purity of a particular compound could be determined.

The term "treating" means to relieve, alleviate, delay, reduce, reverse, improve or prevent at least one symptom of a condition in a subject. The term "treating" may also mean to arrest, delay the onset (i.e., the period prior to clinical manifestation of a disease) and/or reduce the risk of developing or worsening a condition.

An "effective amount" means the amount of a compounds of the present invention that, when administered to a patient (e.g., a mammal) for treating a disease, is sufficient to effect such treatment for the disease, or an amount of a compound that is sufficient for modulating a dopamine receptor (particularly, the dopamine $D_2$ and/or dopamine $D_3$ receptor) to achieve the objectives of the invention. The "effective amount" will vary depending on the compound, the disease and its severity and the age, weight, etc., of the patient to be treated.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

In some embodiments, the compounds of the present invention are administered as a mono-therapy. In other embodiments, the compounds of the present invention are administered as part of a combination therapy. For example, a compound of the invention may be used in combination with other drugs or therapies that are used in the treatment/prevention/suppression or amelioration of the diseases or conditions for which compounds of the invention are useful.

Such other drug(s) may be administered, by a route and in an amount commonly used therefor, contemporaneously or sequentially with a compound of the invention. When a compound of the present invention is used contemporaneously with one or more other drugs, a pharmaceutical unit dosage form containing such other drugs in addition to the compound of the invention may be employed. Accordingly, the pharmaceutical compositions of the present invention include those that also contain one or more other active ingredients, in addition to a compound of invention.

The compounds of the present invention can normally be administered in a daily dosage regimen (for an adult patient)

of, for example, an oral dose between 1 mg and 500 mg, such as between 10 mg and 400 mg, particularly between 10 mg and 250 mg or an intravenous, subcutaneous, or intramuscular dose of between 0.1 mg and 100 mg, such as between 0.1 mg and 50 mg, particularly between 1 and 25 mg of the compound of present invention. The compounds of the present invention can be administered 1 to 4 times per day. The compounds of the present invention can suitably be administered for a period of continuous therapy, for example for a week or more.

Subjects suffering from and in need of treatment of, e.g., schizophrenia or acute mania, as well as the other conditions mentioned above can be treated by the administering a therapeutically effective amount of a compound of formulae (II) and (III) formulated according to, for example and without limitation, the compositions and dosage forms described herein.

Based on their HPLC and MS characterization the compounds of present invention obtained by synthetic methods were shown identical with those found in the biological samples.

The following examples are merely illustrative of the present invention and should not be construed as limiting the scope of the invention in any way as many variations and equivalents that are encompassed by the present invention will become apparent to those skilled in the art upon reading the present disclosure.

EXAMPLES

The metabolites of the present invention were synthetized according to the following procedures:

Example 1

Trans-1-{4-[2-[4-(2,3-dichlorophenyl)-1-oxo-piperazin-1-yl]-ethyl]-cyclohexyl}-3,3-dimethyl-urea (compound D)

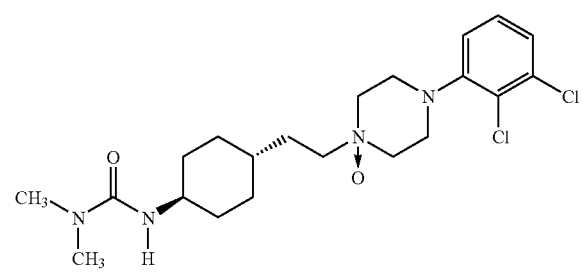 [SMILES: CN(C)C(=O)N[C@H]1CC[C@H](CC[N+]2([O-])CCN(c3cccc(Cl)c3Cl)CC2)CC1]

0.8 g (1.6 mmol) trans-1-{4-[2-[4-(2,3-dichlorophenyl)-piperazin-1-yl]-ethyl]-cyclohexyl}-3,3-dimethyl-urea was dissolved in dichloromethane (60 ml). A solution of 0.54 g (2.4 mmol) 3-chloro-perbenzoic acid in dichloromethane (10 ml) was dropped in and the reaction mixture stirred for 24 hours at room temperature. The reaction was monitored by TLC. The solution was washed twice with saturated NaHCO₃ solution, the organic layer dried and evaporated in vacuo. Flash chromatography gave 0.45 g (63.3%) of the title compound melting at 175-8° C.

Example 2

Trans-1-{4-[2-[4-(2,3-dichloro-4-hydroxy-phenyl)-piperazin-1-yl]-ethyl]-cyclohexyl}-3,3-dimethyl-urea (compound C)

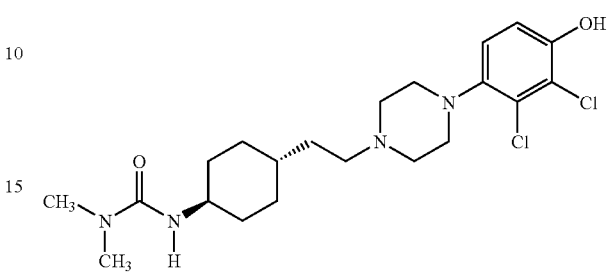

0.92 g (2 mmol) trans-4-{2-[4-(2,3-dichloro-4-methoxy-phenyl)-piperazin-1-yl]-ethyl}-cyclohexyl-amine dihydrochloride was suspended in dichloromethane (60 ml), triethylamine (1.26 ml, 9 mmol) was added followed by 0.21 ml (2.3 mmol) N,N-dimethylcarbamoylchloride. The reaction mixture was stirred for 48 hours at room temperature. The solution was washed with water (2×10 ml), dried and evaporated in vacuo. Purification with flash chromatography gave 0.66 g trans-1-{4-[2-[4-(2,3-dichloro-4-methoxy-phenyl)-piperazin-1-yl]-ethyl]-cyclohexyl}-3,3-dimethyl-urea, melting at 196-8° C. This product was dissolved in dichloromethane (60 ml), then 6.4 ml (6.4 mmol) borontribromid solution (1M in CH₂Cl₂) was dropped in at 5° C. and the mixture stirred at room temperature for 24 hours. The reaction was monitored by TLC. 4 ml methanol was added, followed by 25 ml saturated NaHCO₃ solution. After separation the organic layer was dried and evaporated in vacuo. Purification with flash chromatography gave 0.4 g of the title compound, melting at 278-80° C.

Example 3

Trans-1-{4-[2-[4-(2,3-dichloro-4-hydroxy-phenyl)-piperazin-1-yl]-ethyl]-cyclohexyl}-3-methyl-urea (compound B)

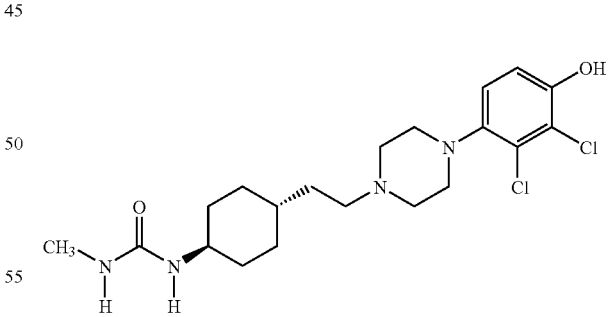

1.38 g (3 mmol) trans-4-{2-[4-(2,3-dichloro-4-methoxy-phenyl)-piperazin-1-yl]-ethyl}-cyclohexyl-amine dihydrochloride was suspended in dry dichloromethane (100 ml), triethylamine (1.72 ml, 12.4 mmol) was added and 0.34 g (1.14 mmol) triphosgene dissolved in dichloromethane was dropped in. After one hour stirring at room temperature methylamine (33% solution in ethanol) was added and the stirring was continued for 20 hours. The mixture was evaporated. 20 ml water was added, the precipitate filtered, washed with water, dried. Recrystallizing the product from methanol gave trans-1-{4-[2-[4-(2,3-dichloro-4-methoxy-phenyl)-piperazin-1-yl]-ethyl]-cyclohexyl}-3-methyl-urea (0.86 g, 65%) melting above 250° C. This product was dissolved in dichloromethane (60 ml), then 10 ml (10 mmol) borontribromid solution (1M in CH$_2$Cl$_2$) was dropped in at 5° C. and the mixture stirred at room temperature for 24 hours. The reaction was monitored by TLC. 4 ml methanol was added and the mixture evaporated. 35 ml saturated NaHCO$_3$ solution was added. The precipitate was filtered, washed with water and dried, recrystallized from methanol giving 0.34 g of title compound, melting at 237-41° C.

Example 4

Trans-1-{4-[2-[4-(2,3-dichloro-4-hydroxy-phenyl)-piperazin-1-yl]-ethyl]-cyclohexyl}-urea (compound A)

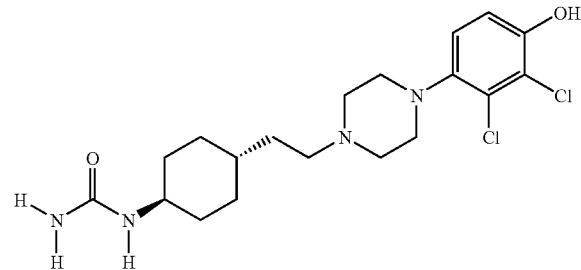 [SMILES: NC(=O)N[C@H]1CC[C@H](CCN2CCN(c3ccc(O)c(Cl)c3Cl)CC2)CC1]

1.38 g (3 mmol) trans-4-{2-[4-(2,3-dichloro-4-methoxy-phenyl)-piperazin-1-yl]-ethyl}-cyclohexyl-amine dihydrochloride was suspended in dry dichloromethane (100 ml), triethylamine 1.72 ml, 12.4 mmol) was added and 0.34 g (1.14 mmol) triphosgene dissolved in dichloromethane was dropped in. After one hour stirring at room temperature ammonia (20% solution in methanol) was added and the stirring was continued for 20 hours. The mixture was evaporated. 20 ml water was added, the precipitate filtered, washed with water, dried. Recrystallizing the product from methanol gave 0.86 g trans-1-{4-[2-[4-(2,3-dichloro-4-methoxy-phenyl)-piperazin-1-yl]-ethyl]-cyclohexyl}-urea melting above 250° C. This product was dissolved in dichloromethane (60 ml), then 10 ml (10 mmol) borontribromid solution (1M in CH$_2$Cl$_2$) was dropped in at 5° C. and the mixture stirred at room temperature for 24 hours. The reaction was monitored by TLC. 4 ml methanol was added and the mixture evaporated. 35 ml saturated NaHCO$_3$ solution was added. The precipitate was filtered, washed with water and dried, recrystallized from methanol giving 0.37 g of title compound, melting at 195-8° C.

Biological Test Methods
Receptor Binding Assays
1. D$_3$ Receptor Binding

Binding assays were carried out on rat recombinant D$_3$ receptors (expressed in Sf9 cells) according to the supplier instructions (Packard BioScience, BioSignal Packard Inc. Cat. No. 6110139, Technical Data Sheet) using [$^3$H]-spiperone (0.85 nM) as ligand and haloperidol (10 μM) for determination of non-specific binding.

2. D$_2$ Receptor Binding

D$_2$ receptor binding assay was carried out as described by Creese et al., *European Journal of Pharmacology*, 60, 55-66, 1979) on rat brain striatal membrane preparation using [$^3$H]-spiperone (0.6 nM) as ligand. The non-specific binding was determined in the presence of 1 μM (+)-butaclamol.

3. Alpha-1 Receptor Binding

Alpha-1 receptor binding study was performed according to the method described by Greengrass and Bremmer (European Journal of Pharmacology 55:323-326, 1979) on rat brain cortical membrane preparation using [$^3$H]-prasosin (0.5 nM) as ligand. The non-specific binding was determined in the presence of 10 μM phentolamine.

D$_3$, D$_2$ and alpha-1 receptor binding data of selected metabolites of the present invention are listed in Table 1 below.

TABLE 1

| Compound | rD3 Ki (nM) | rD2 Ki (nM) | alpha Ki (nM) |
|---|---|---|---|
| Compound A | 0.26 | 8.4 | >>1000 |
| Compound B | 0.24 | 2.49 | >>1000 |
| Compound C | 0.37 | 80.5 | >>1000 |
| Compound D | >>10 | >>100 | >>1000 |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description.

The entire disclosures of all applications, patents and publications, cited above and below, are hereby incorporated by reference in their entirety.

We claim:

1. An isolated or synthesized compound of formula (II):

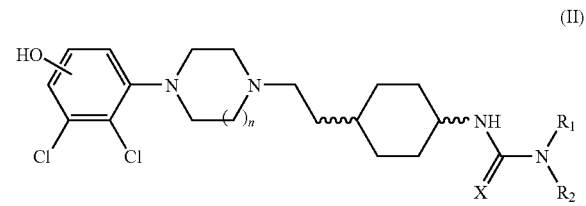

wherein
R$_1$ and R$_2$ are each, independently, hydrogen, alkyl, alkenyl, aryl, cycloalkyl, aroyl or R$_1$ and R$_2$ form a heterocyclic ring with the adjacent nitrogen atom;
X is O or S;
n is 1;
or geometric isomers or stereoisomers or diastereomers or salts or polymorphs thereof.

2. A compound according to claim 1, wherein formula (II) is represented by formula (IIa)

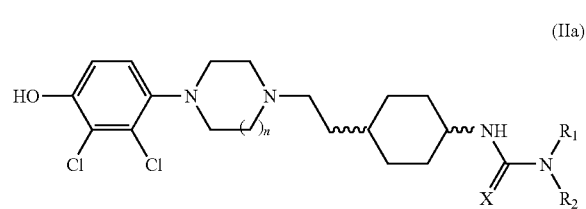

wherein R$_1$, R$_2$, X and n are as defined above for formula (II).

3. A compound according to claim 1, wherein
R$_1$ and R$_2$ are each, independently hydrogen, C$_{1-6}$ alkyl with straight or branched chain optionally substituted with one or more C$_{1-6}$ alkoxycarbonyl, aryl or (C$_{1-6}$ alkoxycarbonyl)-C$_{1-6}$ alkyl group, C$_{2-7}$ alkenyl with 1 to 3 double bonds, a mono-, bi- or tricyclic aryl optionally substituted with one or more $C_{1-6}$ alkoxy, trifluoro $C_{1-6}$ alkoxy, $C_{1-6}$ alkoxycarbonyl, $C_{1-6}$ alkanoyl, aryl, $C_{1-6}$ alkylthio, halogen or cyano, an optionally substituted mono-, bi- or tricyclic cycloalkyl group, aroyl, or $R_1$ or $R_2$ or both $R_1$ and $R_2$ form a heterocyclic ring with the adjacent nitrogen atom, which may be saturated or unsaturated optionally substituted monocyclic or bicyclic ring, which may contain further heteroatoms selected from O, N, and S;

X is oxygen;

n is 1.

4. A compound according to claim 1, wherein $R_1$ and $R_2$ are each, independently hydrogen, $C_{1-6}$ alkyl with straight or branched chain and optionally substituted with one or more $C_{1-6}$ alkoxycarbonyl, phenyl or $(C_{1-6}$ alkoxycarbonyl$)$-$C_{1-6}$ alkyl group, $C_{2-7}$ alkenyl with 1 double bond, phenyl or naphthyl optionally substituted with one or more $C_{1-6}$ alkoxy, trifluoro-$C_{1-6}$ alkoxy, $C_{1-6}$ alkoxycarbonyl, $C_{1-6}$ alkanoyl, aryl, $C_{1-6}$ alkylthio, halogen, cyano, cyclohexyl, adamantyl, benzoyl, or $R_1$ or $R_2$ or both $R_1$ and $R_2$ form a heterocyclic ring with the adjacent nitrogen atom, which may be saturated optionally by $C_{1-6}$ alkyl or hydroxy substituted monocyclic ring, which may contain further heteroatoms selected from O or N;

X is oxygen;

n is 1.

5. A compound according to claim , wherein $R_1$ and $R_2$ are each, independently hydrogen, $C_{1-6}$ alkyl with straight or branched chain optionally substituted with $C_{1-6}$ alkoxycarbonyl or phenyl group, allyl, phenyl optionally substituted with one or more $C_{1-6}$ alkoxy, cyano, $C_{1-6}$ alkanoyl, cyclohexyl, or $R_1$ and/or $R_2$ with the adjacent nitrogen atom an optionally by $C_{1-6}$ alkyl or hydroxy substituted pyrrolidine, piperazine, piperidine or morpholine ring;

X is oxygen;

n is 1.

6. A compound according to claim 1, wherein $R_1$ and $R_2$ are each, independently hydrogen or alkyl;

X is oxygen;

n is 1.

7. A compound selected from

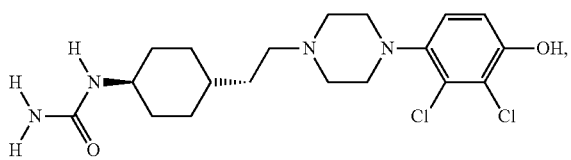

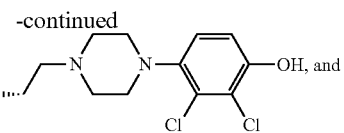

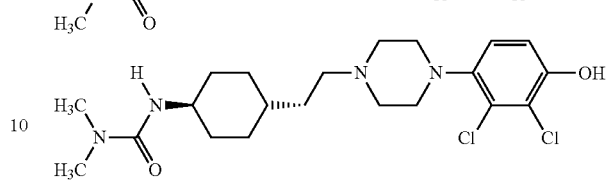

or geometric isomers or stereoisomers or diastereomers or salts or polymorphs thereof.

8. A pharmaceutical composition comprising a compound of formula (II)

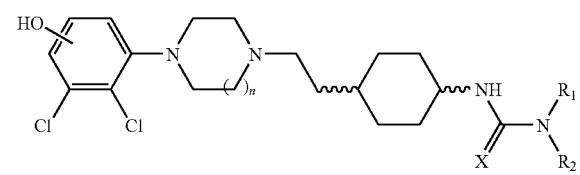

wherein $R_1$ and $R_2$, are each, independently, hydrogen, alkyl, alkenyl, aryl, cycloalkyl, or aroyl, or $R_1$ and $R_2$ form a heterocyclic ring with the adjacent nitrogen atom;

X is O or S;

n is 1 or 2;

or geometric isomers or stereoisomers or diastereomers or salts or polymorphs thereof and one or more pharmaceutically acceptable carrier.

9. A pharmaceutical composition comprising a compound according to claim 7 and one or more pharmaceutically acceptable carriers.

10. A method of inhibiting a dopamine receptor, the method comprising contacting a dopamine receptor with an effective amount of a compound according to claim 1.

11. A method of inhibiting a dopamine receptor according to claim 10 wherein the dopamine receptor is a dopamine $D_3$ receptor, a dopamine $D_2$ receptor, or a combination thereof.

12. A method of claim 10, wherein the contacting is done in vitro.

* * * * *

UNITED STATES PATENT AND TRADEMARK OFFICE
CERTIFICATE OF CORRECTION

PATENT NO. : 8,765,765 B2
APPLICATION NO. : 12/600826
DATED : July 1, 2014
INVENTOR(S) : Eva Againe Csongor et al.

It is certified that error appears in the above-identified patent and that said Letters Patent is hereby corrected as shown below:

On the title page, item 54 and in the specification column 1, lines 1-3 delete the title and insert -- Metabolites of (Thio)Carbamoly-Cyclohexane Derivatives --, therefor;

On the title page, line 1, item 57 (Abstract), please delete "of(thio)-" and insert -- of (thio)- --, therefor;

Page 2, Column 1, line 21, item 56 (Other Publications), please delete "Compunds" and insert -- Compounds --, therefor;

Page 2, Column 1, line 51, item 56 (Other Publications), please delete "Pharamacology," and insert -- Pharmacology, --, therefor;

Page 2, Column 2, line 60, item 56 (Other Publications), please delete "Rogó" and insert -- Rogóz --, therefor;

Page 3, Column 2, line 52, item 56 (Other Publications), please delete "Biobehay." and insert -- Biobehav. --, therefor;

In the claims

Column 15, line 23 (Claim 4), please delete "saturated" and insert -- substituted --, therefor;

Column 15, line 28 (Claim 5), please delete "claim ," and insert -- claim 1, --, therefor;

Column 15, line 33 (Claim 5), before "with" please insert -- form a heterocyclic ring --, therefor;

Column 15, line 34 (Claim 5), please delete "an optionally" and insert -- , which may be optionally substituted --, therefor;

In the claims

Signed and Sealed this
Tenth Day of May, 2016

Michelle K. Lee
*Director of the United States Patent and Trademark Office*

Column 16, line 39 (Claim 8), please delete "carrier" and insert -- carriers --, therefor.